United States Patent

Naskar et al.

Patent Number: 5,155,246
Date of Patent: Oct. 13, 1992

[54] WOOL-WAX SUBSTITUTES

[75] Inventors: Sasanka S. Naskar, Witten; Hans L. Hulsmann, Wetter; Reinhard Pass, Witten, all of Fed. Rep. of Germany

[73] Assignee: Dynamit Nobel Aktiengesellschaft, Troisdorf, Fed. Rep. of Germany

[21] Appl. No.: 102,195

[22] Filed: Sep. 29, 1987

Related U.S. Application Data

[63] Continuation of Ser. No. 933,969, Nov. 24, 1986, abandoned, which is a continuation of Ser. No. 831,742, Feb. 19, 1986, abandoned, which is a continuation of Ser. No. 592,171, Mar. 22, 1984, abandoned, which is a continuation of Ser. No. 314,322, Oct. 23, 1981, abandoned.

Foreign Application Priority Data

Oct. 31, 1980 [DE] Fed. Rep. of Germany ....... 3041073

[51] Int. Cl.$^5$ .................. C11C 3/04; C11C 3/06
[52] U.S. Cl. .................................. 554/213
[58] Field of Search ............ 260/410.7, 410.8; 560/199; 554/213

[56] References Cited

U.S. PATENT DOCUMENTS

| 3,745,033 | 7/1973 | Hutchinson | 106/270 |
| 3,989,728 | 11/1970 | Martin | 260/410 |
| 4,089,879 | 5/1978 | Naskar et al. | 260/410.7 |
| 4,366,100 | 12/1982 | Naskar et al. | 260/410.7 |

FOREIGN PATENT DOCUMENTS 0014308 1/1980 European Pat. Off. .
2605329 8/1976 Fed. Rep. of Germany .

Primary Examiner—Carolyn Elmore
Attorney, Agent, or Firm—Sprung Horn Kramer & Woods

[57] ABSTRACT

A wool-wax substitute and a process for its formation are disclosed where the wool-wax substitute is the product of esterification of 1 mole of a glycerol-polyglycerol mixture with:
(a) from 0.5 to 1.1 moles of a saturated aliphatic monocarboxylic acid having from 6 to 10 carbon atoms, or mixtures thereof;
(b) from 0.5 to 1.1 moles of an unsubstituted straight chained saturated aliphatic monocarboxylic acid having from 16 to 22 carbon atoms, or mixtures thereof;
(c) from 0.0 to 0.6 mole of an aliphatic saturated branched-chain monocarboxylic acid having from 16 to 18 carbon atoms;
(d) from 0.0 to 0.5 mole of a saturated monocarboxylic acid having from 16 to 20 atoms and containing hydroxyl groups, or mixtures thereof, and
(e) from 0.5 to 1.0 mole of saturated aliphatic dicarboxylic acids having from 4 to 10 carbon atoms, or mixtures thereof.

The wool-wax has a hydroxyl number ranging from 20 to 100 and acid and iodine numbers under 5.

16 Claims, No Drawings

WOOL-WAX SUBSTITUTES

This is a continuation of application Ser. No. 06/933,969, filed Nov. 24, 1986, now abandoned, which in turn is a continuation of application Ser. No. 831,742, filed Feb. 19, 1986, now abandoned, which in turn is a continuation of application Ser. No. 592,171, filed Mar. 22, 1984, now abandoned, which in turn is a continuation of application Ser. No. 314,322, filed Oct. 23, 1981, now abandoned.

BACKGROUND OF THE INVENTION

1. Field of the Invention

The invention relates to wool-wax substitutes based on homogeneous ester mixtures of products of esterification of glycerol-polyglycerol mixtures with selected mixtures of saturated aliphatic monocarboxylic acids and dicarboxylic acids, said ester mixtures having hydroxyl numbers ranging from 20 to 100, and acid and iodine numbers under 5, as well as to a process for their preparation.

2. Discussion of Prior Art

The object of the invention is the preparation of wool-wax substitutes based on homogeneous ester mixtures whose skin-application behavior is comparable to that of natural wool wax and which can be prepared from industrially available and physiologically satisfactory raw materials. The ester mixtures prepared in accordance with the invention are suitable for use especially in the cosmetic and pharmaceutical fields and also in industrial applications as lubricant auxiliaries and plasticizers for adhesives and resins.

Wool wax, also known as lanolin, is a relatively expensive natural product. Obtaining it and purifying it are costly. The composition of wool wax can vary according to its geographic origin and the feeding conditions of the sheep. A drawback is that it frequently contains pesticides.

Contamination by detergents, bleaches, and aldehydes and ketones formed during the oxidizing treatment of the wool wax reduces the quality of the natural product. In recent years wool wax has come to be suspected as the cause of allergic reactions in sensitive skin.

Natural wool wax is a substance of complex composition. It is essentially a mixture of about 95% esters of higher fatty acids such as hydroxy-fatty acids, straight-chain and branched-chain monocarboxylic acids having from 10 to 31 carbon atoms, and cholesterol, dihydroxycholesterol and isocholesterol, aliphatic higher alcohols having from 16 to 30 carbon atoms, and higher-molecular-weight diols, in addition to small amounts of free paraffinic hydrocarbons, free acids and free alcohols.

Wool wax is obtained from sheep's wool by extraction or scouring processes. The crude product is purified in stages, bleached and deodorized and then forms a pale-yellow, viscous substance having a faint odor. Purified wool wax exhibits an excellent skin-application behavior and has been valued since time immemorial as a component of pharmaceutical and cosmetic preparations.

SUMMARY OF THE INVENTION

The invention has as its object wool-wax substitutes based on homogeneous ester mixtures and characterized by products of esterification of 1 mole of a glycerol-polyglycerol mixture with (a) from 0.5 to 1.1 moles of a saturated aliphatic monocarboxylic acid having from 6 to 10 carbon atoms, or mixtures thereof, (b) from 0.5 to 1.1 moles of an unsubstituted, straight chained saturated aliphatic monocarboxylic acid having from 16 to 22 carbon atoms or mixtures thereof, (c) from 0.0 to 0.6 mole of an unsubstituted aliphatic saturated branched-chain monocarboxylic acid having from 16 to 18 carbon atoms, (d) from 0.0 to 0.5 mole of a saturated monocarboxylic acid having from 16 to 20 carbon atoms and containing hydroxyl groups, or mixtures thereof, and (e) from 0.5 to 1.0 mole of saturated aliphatic dicarboxylic acids having from 4 to 10 carbon atoms, or mixtures thereof, with a hydroxyl number ranging from 20 to 100 and acid and iodine numbers under 5.

The wool-wax substitutes in accordance with the invention possess very good water absorptivity and emulsifiability. Many of the wool-wax substitutes which have been prepared, and particularly those within the preferred range, have water numbers ranging from 100 to 260 and thus exceed the water absorption of good wool waxes.

The emulsifiability of the wool-wax substitutes and the stability of emulsions made from them are comparable to those of wool wax and may be regarded as good.

The products have a viscous, filamentous consistency which corresponds to the "threadiness" that is characteristic of wool wax.

The skin-application behavior, that is to say, the property of forming a film on the skin, of the wool-wax substitutes developed is comparable to that of the natural product.

The tackiness of the new products is preserved even after several months' storage. Various cosmetic preparations based on the substitutes produced in accordance with the invention are equal or superior to preparations made from wool wax even after prolonged storage.

The invention has as a further object a process for the preparation of wool-wax substitutes based on homogeneous ester mixtures which is characterized in that every mole of a glycerol-polyglycerol mixture is esterified with (a) from 0.5 to 1.1 moles of a saturated aliphatic monocarboxylic acid having from 6 to 10 carbon atoms, or mixtures thereof; (b) from 0.5 to 1.1 moles of an unsubstituted, straight chained saturated aliphatic monocarboxylic acid having from 16 to 22 carbon atoms, or mixtures thereof; (c) from 0.0 to 0.6 mole of an unsubstituted aliphatic, saturated, branched-chain monocarboxylic acid having from 16 to 18 carbon atoms, or mixtures thereof; and (d) from 0.0 to 0.5 mole of a saturated monocarboxylic acid having from 16 to 20 carbon atoms and containing hydroxyl groups, or mixtures thereof, at from 200° to 250° C., preferably under a vacuum, to hydroxyl-containing partial esters until an acid number under 50, and preferably under 10, is obtained, and then is further esterified with (e) from 0.5 to 1.0 mole of an aliphatic saturated dicarboxylic acid having from 4 to 10 carbon atoms, or mixtures thereof, at from 200° to 250° C., preferably under a vacuum, until a hydroxyl number ranging from 20 to 100 and an acid number under 5, and preferably under 1, are obtained. The crude product can then be deodorized by conventional means, if desired.

The wool-wax substitutes in accordance with the invention are formed of an aliphatic ester mixture in whose composition, based on the hydroxyl numbers specified, the sum of the acid moieties is always less than the sum of the hydroxyl moieties of the glycerol-polyglycerol mixture. Consistent with acid numbers under 5, and preferably under 1, the esterification of the acids is carried to completion. A low iodine number under 5, and preferably under 1, is assured by the use of saturated acids and low contents of unsaturated acids.

The products of esterification preferably contain per mole of the glycerol-polyglycerol mixture from 0.7 to 1.0 mole of component (a), from 0.7 to 1.0 mole of component (b), from 0.05 to 0.4 mole of the branched-chain monocarboxylic acid (c), from 0.05 to 0.3 mole of the hydroxycarboxylic acid (d), and from 0.60 to 0.9 mole of component (e).

The acids of component (a) are preferably unsubstituted. The acids of component (d) are hydroxy substituent and preferably are otherwise unsubstituted.

It is preferred that the acids used for the esterification contain at least the specified small amounts of the branched-chain monocarboxylic acid (c) and/or the hydroxy carboxylic acid (d), as their use results in improved products for a number of purposes.

An important constituent is the glycerol-polyglycerol mixture. In addition to glycerol, it contains amounts of di- and triglycerol formed by condensation, and of higher condensed glycerol.

The average molecular weight of the glycerol-polyglycerol mixture ranges from 140 to 210, and preferably from 160 to 180, as determined by means of a vapor-pressure osmometer. The viscosity, measured at 65° C., ranges from 300 to 500 mPas.

Glycerol-polyglycerol mixtures can be prepared by condensation of glycerol at temperatures ranging from 240° to 260° C., for example, and pressures ranging from 300 to 600 millibars, for example, using sodium methylate, for example, as a catalyst. Components (a) and (b) are straight-chain fatty acids. Mixtures are preferably used as component (a), and in particular the coconut first-runnings fatty acid obtained in the distillation of coconut fatty acid, which contains from 0.3 to 3.0 weight percent $C_6$, from 50 to 65 weight percent $C_8$, from 30 to 50 weight percent $C_{10}$ and from 1.0 to 3.0 weight percent $C_{12}$ acid, and preferably from 0.4 to 1.3 weight percent $C_6$, from 52 to 64 weight percent $C_8$, from 32 to 46 weight percent $C_{10}$ and from 1.8 to 2.6 weight percent $C_{12}$ acid. Preferred for use as component (b) are palmitic acid and especially stearic acid and mixtures thereof. Generally speaking, the acids used for components a, b, c, d, and e, are alkanoic acids, normally unsubstituted, except for the hydroxy group(s) on component d.

The so-called isostearic acid is used as component (c). It is a mixture of many isomeric, primarily methyl-branched $C_{18}$ fatty acids with low iodine numbers and hence but slight tendency to oxidize. (H. Janistyn, Handbuch der Kosmetika und Riechstoffe [Handbook of Cosmetics and Perfumes], vol. 1, p. 533. Manufacturer: Unilever Emmery N. V., Condea, Netherlands.)

Preferred for use as component (d) are hydroxy acids containing a hydroxyl group, and in particular 12-hydroxystearic acid, while succinic acid, adipic acid and sebacic acid are preferred for use as component (e).

The new wool-wax substitutes have the advantages of homogeneous ester mixtures, whose properties can be adapted to the contemplated end use. They are, therefore, suited for all cosmetic, pharmaceutical and also industrial uses where wool wax is now employed.

It will be appreciated that the instant specification and examples which follow are set forth by way of illustration and not of limitation, and that various changes and modifications may be made without departing from the spirit and scope of the present invention.

EXAMPLE 1

In a three-neck flask equipped with agitator, water separator, dephlegmator, thermometer and gas inlet pipe, a mixture of 186.8 g (1.10 moles) of a glycerol-polyglycerol mixture of an average molecular weight of 170, (a) 107.8 g (0.691 mole) coconut first-runnings fatty acid (composition, 0.5 wt. % $C_6$, 62.5 wt. % $C_{10}$, 35.0 wt. % $C_8$ and 2.0 wt. % $C_{12}$ acid), (b) 257.8 g (0.906 mole) stearic acid, (c) 113.8 g (0.4 mole) isostearic acid, and (d) 30.1 g (0.1 mole) 12-hydroxystearic acid and 0.5 g isopropyl titanate is heated over 2 hours to 240° C. at 400 millibars with agitation under a stream of inert gas and the water of reaction is eliminated until an acid number of less than 10 is obtained. The content of the flask is then cooled to 140° C. After the addition of (e) 116.8 g (0.8 mole) adipic acid, the mixture is heated to 240° C. with agitation and under inert gas, the water of reaction forming being simultaneously removed. Esterification is then carried out until an acid number under 2 is obtained, the vacuum being gradually increased to 5 millibars. The crude ester so obtained is conventionally deodorized and filtered.

| Characteristic values: | Acid number | 0.5 |
| --- | --- | --- |
| | Saponification number | 283 |
| | Hydroxyl number | 60 |

EXAMPLE 2

By the procedure given in Example 1, 186.8 g (1.1 moles) of a glycerol-polyglycerol mixture of an average molecular weight of 170 is esterified with (a) 142.9 g (0.916 mole) coconut first-running fatty acid (composition, 0.5 wt. % $C_6$, 62.5 wt. % $C_8$, 35.0 wt. % $C_8$ and 2.0 wt. % $C_{12}$ acid), (b) 222.3 g (0.781 mole) stearic acid, (c) 113.4 g (0.4 mole) isostearic acid, (d) 30.1 g (0.1 mole) 12-hydroxystearic acid and (e) 102.2 g (0.7 mole) adipic acid.

| Characteristic values: | Acid number | 0.75 |
| --- | --- | --- |
| | Saponification number | 278 |
| | Hydroxyl number | 58 |

EXAMPLE 3

By the procedure given in Example 1, 186.8 g (1.1 mole) of a glycerol-polyglycerol mixture of an average molecular weight of 170 is esterified with (a) 131.2 g (0.841 mole) coconut first-runnings fatty acid (composition, 0.5 wt. % $C_6$, 62.5 wt. % $C_8$, 35.0 wt. % $C_8$ and 2.0 wt. % $C_{12}$ acid), (b) 273.5 g (0.961 mole) stearic acid, (c) 42.6 g (0.15 mole) isostearic acid, (d) 45.1 g (0.15 mole) 12-hydroxystearic acid and (e) a dicarboxylic acid mixture formed of 35.4 g (0.3 mole) succinic acid, 43.8 g (0.3 mole) adipic acid and 30.3 g (0.15 mole) sebacic acid.

| Characteristic values: | Acid number | 1.0 |
| --- | --- | --- |
| | Saponification number | 278 |
| | Hydroxyl number | 71 |

EXAMPLE 4 (use)

Example of a basic pharmaceutical formula for an ointment in which natural wool wax may be replaced with the synthetic wool-wax substitute obtained in Example 3 without altering the properties

| | |
|---|---|
| Peanut oil | 15% |
| Paraffin liq. | 21% |
| Vaseline | 22% |
| Paraffin, hard | 7% |
| Borax | 0.3% |
| Wool wax or wool-wax substitute | 5% |
| Distilled water | ad 100% |

What is claimed is:

1. A wool-wax substitute based on homogeneous ester mixtures, which is the esterification product obtained by esterifying the partial esterification product of a glycerol-polyglycerol mixture having a molecular weight of 140 to 210 with
   (a) from 0.7 to 1.0 moles, per mole of said glycerol-polyglycerol mixture, of coconut first-running fatty acids obtained in the distillation of coconut fatty acids, which contain from 0.3 to 3.0 weight percent $C_6$, from 50 to 65 weight percent $C_8$, from 30 to 50 weight percent $C_{10}$ and from 1.0 to 3.0 weight percent $C_{12}$,
   (b) from 0.7 to 1.0 moles, per mole of said glycerol-polyglycerol mixture, of an unsubstituted straight chain saturated aliphatic monocarboxylic acid selected from the group consisting of palmitic acid, stearic acid and mixtures thereof,
   (c) from 0.05 to 0.4 mol, per mol of said glycerol-polyglycerol mixture, of isostearic acid;
   (d) from 0.05 to 0.3 mol, per mole of said glycerol-polyglycerol mixture, of a hydroxy stearic acid with
   (e) from 0.60 to 0.9 mol, per mole of said glycerol-polyglycerol mixture, of a saturated aliphatic dicarboxylic acid selected from the group consisting of succinic acid, adipic acid, sebacic acid and mixtures thereof,
   the wool-wax substitute having a hydroxyl number ranging from 20 to 100, an acid number under 5 and an iodine number under 5.

2. A wool-wax substitute according to claim 1, wherein said glycerol-polyglycerol mixture itself has a viscosity, measured at 65° C., ranging from 300 to 500 mPas.

3. A wool-wax substitute according to claim 1, having an iodine number under 1.

4. A wool-wax substitute according to claim 1, which is the product of said esterification, the sum of the acid moieties in the esterification being less than the sum of the hydroxyl moieties of the glycerol-polyglycerol mixture.

5. A wool-wax substitute according to claim 4, having an acid number under 1.

6. A wool-wax substitute according to claim 1, wherein for (a), the coconut first-running fatty acids contain 0.4 to 1.3 weight percent $C_6$, from 52 to 64 weight percent $C_8$, from 32 to 46 weight percent $C_{10}$ and from 1.8 to 2.6 weight percent $C_{12}$.

7. A wool-wax substitute according to claim 1, wherein (a) is a coconut first-running fatty acid comprising 0.5 weight percent $C_6$, 62.5 weight percent $C_{10}$, 35.0 weight percent $C_8$ and 2.0 weight percent $C_{12}$.

8. A wool-wax substitute according to claim 1, wherein (b) is stearic acid.

9. A wool-wax substitute according to claim 1, wherein (e) is adipic acid.

10. A wool-wax substitute according to claim 1, wherein (d) is 12-hydroxystearic acid.

11. A wool-wax substitute according to claim 1, wherein (e) is a mixture of succinic acid, adipic acid and sebacic acid.

12. A wool-wax substitute according to claim 1, wherein said wool wax has a viscous, filamentous consistency that is characteristic of natural wool-wax.

13. A wool-wax substitute according to claim 1, wherein said glycerol-polyglycerol mixture has a molecular weight of 160 to 180.

14. A wool-wax substitute according to claim 1, which form a film on the skin.

15. A wool-wax substitute based on homogeneous ester mixtures, which is the esterification product obtained by esterifying the partial esterification product of a glycerol-polyglycerol mixture having a molecular weight of 140 to 210 with (a) from 0.5 to 1.1 moles, per mole of said glycerol-polyglycerol mixture, of a saturated aliphatic monocarboxylic acid having from 6 to 10 carbon atoms, or mixtures thereof, (b) from 0.5 to 1.1 moles, per mole of said glycerol-polyglycerol mixture, of an unsubstituted straight chained saturated aliphatic monocarboxylic acid having from 16 to 22 carbon atoms, or mixtures thereof, (c) from 0.0 to 0.6 mole of, per mole of said glycerol-polyglycerol mixture, of an aliphatic saturated branched-chain monocarboxylic acid having from 16 to 18 carbon atoms, (d) from 0.0 to 0.5 mole, per mole of said glycerol-polyglycerol mixture, of a saturated monocarboxylic acid having from 16 to 20 atoms and containing hydroxyl groups, or mixtures thereof, with (e) from 0.5 to 1.0 mole, per mole of said glycerol-polyglycerol mixture, of saturated aliphatic dicarboxylic acids having from 4 to 10 carbon atoms, or mixtures thereof, the wool-wax substitute having a hydroxyl number ranging from 20 to 100, an acid number under 5 and an iodine number under 5.

16. A wool-wax substitute according to claim 1, wherein (b) is 0.9 to 1.0 moles, per mole of said glycerol-polyglycerol mixture, (c) is 0.4 moles, per mole of said glycerol-polyglycerol mixtures and (d) is 0.1 to 0.3 moles, per mole of said glycerol-polyglycerol mixture.

* * * * *